United States Patent

(12) United States Patent
Arai et al.

(10) Patent No.: US 10,226,224 B2
(45) Date of Patent: Mar. 12, 2019

(54) MEDICAL IMAGING DEVICE, TUBE VOLTAGE SETTING DEVICE, IMAGING CONTROL METHOD, AND RECORDING MEDIUM STORING IMAGING CONTROL PROGRAM

(71) Applicant: FUJIFILM CORPORATION, Minato-ku, Tokyo (JP)

(72) Inventors: Takahisa Arai, Kanagawa (JP); Tomonari Sendai, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 246 days.

(21) Appl. No.: 15/352,595

(22) Filed: Nov. 16, 2016

(65) Prior Publication Data
US 2017/0245823 A1 Aug. 31, 2017

(30) Foreign Application Priority Data

Feb. 29, 2016 (JP) ................... 2016-037685

(51) Int. Cl.
*A61B 6/00* (2006.01)
*A61B 8/00* (2006.01)
(52) U.S. Cl.
CPC ............ *A61B 6/5247* (2013.01); *A61B 8/469* (2013.01)
(58) Field of Classification Search
CPC .................................................. A61B 6/5247
See application file for complete search history.

(56) References Cited

U.S. PATENT DOCUMENTS 5,664,573 A * 9/1997 Shmulewitz ........... A61B 6/502
128/915
2005/0288581 A1 12/2005 Kapur et al.

FOREIGN PATENT DOCUMENTS

JP    H11-299765 A    11/1999
JP    2005-270677 A   10/2005
JP    2009-082399 A    4/2009

OTHER PUBLICATIONS

English language translation of the following: Office action dated Jan. 22, 2019 from the JPO in a Japanese patent application No. 2016-037685 corresponding to the instant patent application. This office action translation is submitted now in order to supplement the understanding of the cited references which are bein disclosed in the instant Information Disclosure Statement.

* cited by examiner

*Primary Examiner* — Dani Fox
(74) *Attorney, Agent, or Firm* — SOLARIS Intellectual Property Group, PLLC

(57) ABSTRACT

A medical imaging device that includes: a press plate that presses a breast; an emitter that radiates radiation onto the breast; an acquisition section that acquires various information indicating a type of an acoustic matching member inserted between the press plate and the breast in cases in which ultrasound imaging of the breast is performed; and a setting section that sets a tube voltage of the emitter to a first tube voltage, in cases in which radiographic imaging of the breast is performed alone, and that sets the tube voltage of the emitter to a second tube voltage that is different from the first tube voltage, by employing the various information acquired by the acquisition section, in cases in which radiographic imaging and ultrasound imaging of the breast are performed consecutively with the acoustic matching member still inserted.

13 Claims, 13 Drawing Sheets

FIG.8

| TUBE VOLTAGE PRIOR TO CHANGING (kV) | DEVICE SPECIFIC HALF VALUE LAYER (mmAl) | MODEL NUMBER OF ACOUSTIC MATCHING MEMBER (42A) | TUBE VOLTAGE AFTER CHANGING (kV) |
|---|---|---|---|
| ⋮ | ⋮ | | ⋮ |
| 25 | 0.54 | | 22 |
| ⋮ | ⋮ | 1 | ⋮ |
| 28 | 0.56 | | 25 |
| ⋮ | ⋮ | | ⋮ |
| 31 | 0.58 | | 28 |
| ⋮ | ⋮ | | ⋮ |
| ⋮ | ⋮ | | ⋮ |
| 25 | ⋮ | 2 | ⋮ |
| ⋮ | ⋮ | | ⋮ |
| ⋮ | ⋮ | | ⋮ |
| 25 | ⋮ | 3 | ⋮ |
| ⋮ | ⋮ | | ⋮ |
| ⋮ | ⋮ | ⋮ | ⋮ |

FIG.9

| TUBE VOLTAGE AFTER CHANGING (kV) | MODEL NUMBER OF ACOUSTIC MATCHING MEMBER | DOSE CORRECTION COEFFICIENT |
|---|---|---|
| ⋮ | | ⋮ |
| 22 | | 1/0.85 |
| ⋮ | | ⋮ |
| 25 | 1 | 1/0.9 |
| ⋮ | | ⋮ |
| 28 | | 1/0.95 |
| ⋮ | | ⋮ |
| ⋮ | | ⋮ |
| 22 | 2 | ⋮ |
| ⋮ | | ⋮ |
| ⋮ | | ⋮ |
| 22 | 3 | ⋮ |
| ⋮ | | ⋮ |
| ⋮ | ⋮ | ⋮ |

42B

MEDICAL IMAGING DEVICE, TUBE VOLTAGE SETTING DEVICE, IMAGING CONTROL METHOD, AND RECORDING MEDIUM STORING IMAGING CONTROL PROGRAM

CROSS-REFERENCE TO RELATED APPLICATION

This application claims priority under 35 USC 119 from Japanese Patent Application No. 2016-037685, filed on Feb. 29, 2016, the entire contents of which are incorporated herein by reference.

FIELD

The present disclosure relates to a medical imaging device, a tube voltage setting device, an imaging control method, and a recording medium storing an imaging control program.

BACKGROUND

There are cases in which breast examinations, diagnoses, etc. are performed using both radiographic imaging and ultrasound imaging. When performing radiographic imaging of a breast using an ordinary mammography machine, the breast of an examinee is placed in a pressed state using a press plate. However, when performing ultrasound imaging of a breast using an ordinary ultrasound imaging device, imaging is performed by an operator moving an ultrasound probe over the surface of the breast of an examinee. It is sometimes difficult, for example, to observe the site of interest when comparing both images due to differences in the pressed state of the breast of an examinee, and the imaging state etc. between when performing radiographic imaging and when performing ultrasound imaging. There is accordingly a desire for a medical imaging device capable of performing both radiographic imaging and ultrasound imaging, and, for example, technology is described in Japanese Patent Application Laid-Open (JP-A) Nos. 2009-082399 and 2005-270677.

In the technology described in JP-A Nos. 2009-082399 and 2005-270677, an ultrasound image and a radiographic image are acquired in which the pressed state of the breast of an examinee, and the imaging state, etc. have been made the same, by performing radiographic imaging and ultrasound imaging in a pressed state of the breast of a single examinee using a single medical imaging device. This facilitates observation of the site of interest and so on in a comparison of the radiographic image and the ultrasound image of the same breast.

Generally, when performing ultrasound imaging, in order to reduced non-uniformity in the impedance of ultrasound waves, an acoustic matching member is inserted between the ultrasound probe and the breast. When performing radiographic imaging in a state in which an acoustic matching member has been inserted, radiation that has passed through the acoustic matching member is incident to the breast. Thus, for example, the characteristics of the radiation incident to the breast is sometimes different to that of radiation incident to the breast without passing through the acoustic matching member.

SUMMARY

A medical imaging device of the present disclosure includes a press plate that presses a breast, an emitter that radiates radiation onto the breast, an acquisition section that acquires various information indicating a type of an acoustic matching member inserted between the press plate and the breast in cases in which ultrasound imaging of the breast is performed, and a setting section. The setting section sets a tube voltage of the emitter to a first tube voltage in cases in which radiographic imaging of the breast is performed alone, and that sets the tube voltage of the emitter to a second tube voltage different from the first tube voltage by employing the various information acquired by the acquisition section in cases in which radiographic imaging and ultrasound imaging of the breast are performed consecutively with the acoustic matching member still inserted.

BRIEF DESCRIPTION OF DRAWINGS

FIG. 8 is diagram illustrating an example of a tube voltage change table.

FIG. 9 is a diagram illustrating an example of a dose change table.

DETAILED DESCRIPTION OF THE INVENTION

Detailed explanation follows regarding exemplary embodiments of the present disclosure, with reference to the drawings. Note that the present disclosure is not limited to the present exemplary embodiments.

First Exemplary Embodiment

Figure 1:
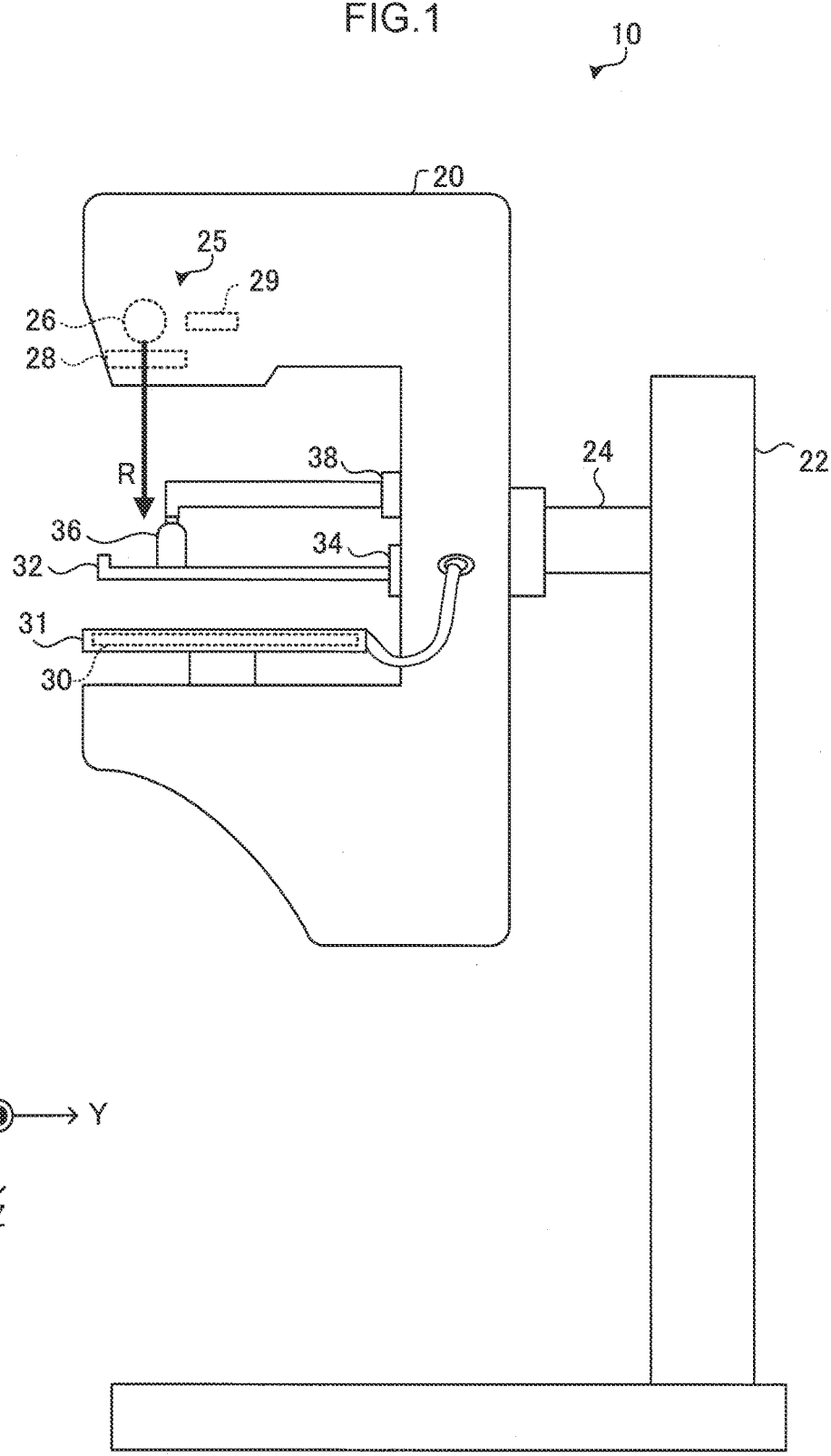
FIG. 1 is a side view illustrating the external appearance of an imaging section of a medical imaging device of a first exemplary embodiment.

First, explanation follows regarding a configuration of a medical imaging device according to the present exemplary embodiment, with reference to FIG. 1.

A medical imaging device 10 of the present exemplary embodiment combines functionality of a radiographic mammography machine that performs radiographic imaging by radiating radiation R onto a breast of a subject and detecting the radiation R that has passed through the breast, and functionality of a ultrasound imaging device that performs ultrasound imaging by transmitting ultrasound waves through the breast of a subject, and receiving an ultrasound echo reflected by the interior of the breast.

As illustrated in FIG. 1, the medical imaging device 10 of the present exemplary embodiment includes an arm 20, a stand 22, and a shaft 24. The stand 22 holds the arm 20 so that the arm 20 is movable in the up-down direction (the Z axis direction). The shaft 24 connects the arm 20 to the stand 22. The arm 20 is able to rotate relative to the stand 22 about a rotation axis of the shaft 24.

A radiation emitter 25, an imaging table 31, a press plate 32, a press plate moving mechanism 34, an ultrasound probe 36, and a probe moving mechanism 38 are provided to the arm 20.

The radiation emitter 25 includes a radiation tube 26, a filter 28, and a high voltage generator 29. The radiation tube 26 generates radiation R by application of a tube voltage. The filter 28 is formed from a material such as molybdenum (MO) or rhodium (Rh), and selectively allows desired wavelength components, from out of plural wavelength components contained in the radiation R generated by the radiation tube 26, to pass through.

In order to perform imaging, the breast of an examinee is positioned on the imaging table 31. From the perspectives of transmissivity to radiation R and strength, the imaging table 31 and the like that the breast of the examinee contacts are formed from a carbon composite, for example. A radiation detector 30 is disposed inside the imaging table 31 for detecting radiation R that has passed through the breast and the imaging table 31. Radiographic imaging is generated based on the radiation R detected by the radiation detector 30. There are no particular limitations to the type of the radiation detector 30 of the present exemplary embodiment, and, for example, an indirect conversion type of radiation detector may be employed that converts radiation R into light and then converts the converted light into charge, or a direct conversion type of radiation detector may be employed that converts the radiation R directly into charge.

The press plate 32 is moved in the up-down direction (the Z axis direction) by the press plate moving mechanism 34, and presses the breast of the examinee against the imaging table 31. The press plate 32 is preferably optically transparent in order to confirm positioning and the pressed state during pressing of the breast, and is formed from a material having excellent transmissivity to the radiation R in order to readily transmit the radiation R emitted from the radiation emitter 25. The press plate 32 is also preferably formed from a material that readily propagates ultrasound waves transmitted from the ultrasound probe 36. Examples of materials that may be employed for the press plate 32 include resins such as polymethylpentene, polycarbonate, acrylic, and polyethylene terephthalate. Polymethylpentene is particularly appropriately employed as the material of the press plate 32 due to having a low rigidity, excellent extensibility and flexibility, and also having appropriate values of sound impedance, which influences the reflectivity of ultrasound waves, and attenuation coefficient, which influences ultrasound wave attenuation.

The ultrasound probe 36 is moved along the upper face of the press plate 32 (the face on the opposite side to the side where the breast of the examinee is disposed) by the probe moving mechanism 38, and acquires an ultrasound image of the breast by scanning the breast with ultrasound waves. The ultrasound probe 36 includes plural ultrasound transducers arrayed in one dimension or in two dimensions. Each of the ultrasound transducers transmits ultrasound waves according to a drive signal applied thereto, and outputs a reception signal by receiving an ultrasound echo.

Each of the plural ultrasound transducers is, for example, configured by a vibration element having electrodes formed on both ends of a material having piezoelectric properties (a piezoelectric body), such as a piezoelectric ceramic as typified by Pb (lead) zirconate titanate (PZT), or a polymer piezoelectric element as typified by polyvinylidene difluoride (PVDF). The piezoelectric body expands and contracts when a drive signal of a pulse shape or a continuous wave is transmitted to the electrodes of the vibration element and a voltage is applied thereto. Pulse shaped or continuous wave ultrasound waves are generated from the respective vibration elements by the expansion and contraction, and an ultrasound wave beam is formed by these ultrasound waves combining. The respective vibration elements also expand and contract on receiving propagating ultrasound waves, and generate an electrical signal. These electrical signals are output as ultrasound reception signals, and are input to a controller 40 (see FIG. 2) through a cable.

In order to perform ultrasound imaging, the ultrasound probe 36 is moved along the upper face of the press plate 32 in a state in which the upper face of the press plate 32 has been coated in an acoustic matching member such as an echo jelly (described in detail below, see FIG. 6). In the medical imaging device 10 of the present exemplary embodiment, ultrasound imaging is performed automatically, without an operator moving the ultrasound probe 36, by the controller 40 (see FIG. 2) moving the ultrasound probe 36 using the probe moving mechanism 38. Note that there is no limitation to the present exemplary embodiment, and ultrasound imaging may be performed by an operator moving the ultrasound probe 36.

Figure 2:
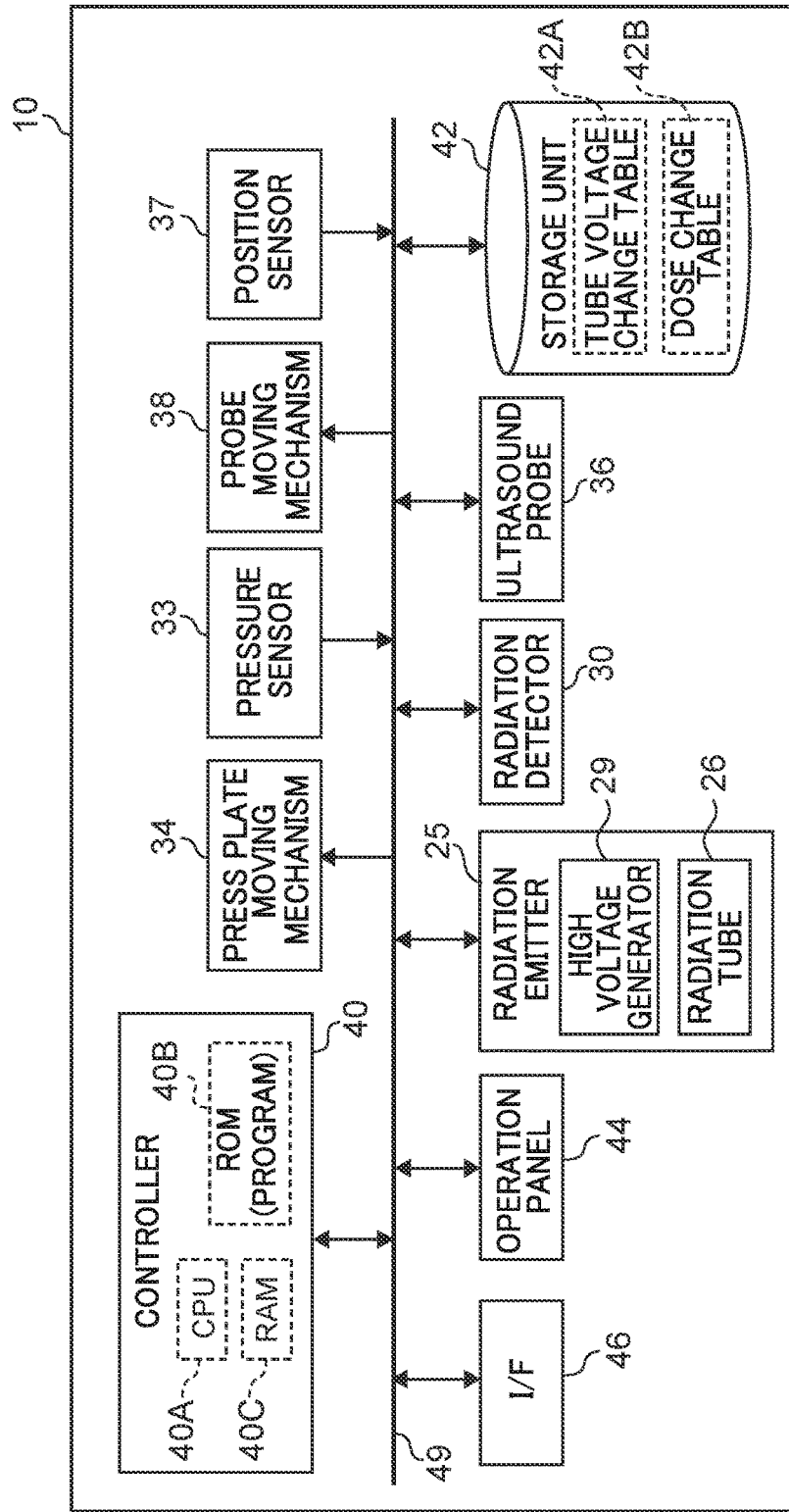
FIG. 2 is a block diagram illustrating a configuration of a medical imaging device of the first exemplary embodiment.

As illustrated in FIG. 2, the medical imaging device 10 of the present exemplary embodiment also includes a pressure sensor 33, a position sensor 37, the controller 40, a storage unit 42, an operation panel 44, and an interface (I/F) 46. The radiation emitter 25, the radiation detector 30, the pressure sensor 33, the press plate moving mechanism 34, the ultrasound probe 36, the position sensor 37, the probe moving mechanism 38, the controller 40, the storage unit 42, the operation panel 44, and the interface (I/F) 46 are connected together by a bus 49, such as a system bus or a control bus, so as to be capable of exchanging various signals with each other.

The controller 40 includes a central processing unit (CPU) 40A, read only memory (ROM) 40B, and random access memory (RAM) 40C. Various programs, etc. to be executed by the CPU 40A are pre-stored in the ROM 40B. The RAM 40C temporarily stores various data.

The pressure sensor 33 detects pressure applied to the press plate 32. The position sensor 37 is internally installed in the ultrasound probe 36, and detects the position of the ultrasound probe 36 (the position on the surface of the press plate 32).

The controller 40 controls the overall operation of the medical imaging device 10. The controller 40 of the present exemplary embodiment controls the radiation emitter 25, the radiation detector 30, and the press plate moving mechanism 34 to perform radiographic imaging. Based on the detection results of the pressure sensor 33, the controller 40 uses the press plate moving mechanism 34 to move the press plate 32 and press the breast against the imaging table 31. The controller 40 causes the radiation R to be emitted from the radiation tube 26 by the radiation emitter 25. The transmissivity to the radiation R is determined by the tube voltage applied between the cathode and the anode of the radiation tube 26. The amount of radiation R generated, namely, the dose of the radiation R radiated onto the breast, is determined by the integral value of the tube current flowing between the cathode and the anode of the radiation tube 26 with respect to time (also sometimes referred to as the mAs value). Thus the controller 40 adjusts the imaging conditions, such as the tube voltage and the tube current, such that the radiation R is emitted from the radiation emitter 25 by applying a high voltage generated by the high voltage generator 29 to the radiation tube 26. The controller 40 performs radiographic imaging by using the radiation detector 30 to detect the radiation R that has passed through the breast.

In order to perform ultrasound imaging, the controller 40 of the present exemplary embodiment controls the ultrasound probe 36 and the probe moving mechanism 38. The controller 40 acquires the position of the ultrasound probe 36 based on the detection results of the position sensor 37, and uses the probe moving mechanism 38 to move the ultrasound probe 36. The controller 40 performs ultrasound imaging by transmitting and receiving ultrasound waves, while moving the ultrasound probe 36 with the probe moving mechanism 38.

The respective image data of the radiographic images and the ultrasound images obtained by imaging, and/or various other data, is stored in the storage unit 42. Examples of the storage unit 42 include a hard disk drive (HDD) and a solid state drive (SSD). A tube voltage change table 42A and a dose change table 42B (see FIG. 8 and FIG. 9, both of which are described in detail below) are stored in the storage unit 42 of the present exemplary embodiment.

The operation panel 44 receives instructions relating to imaging (such as instructions to press the breast with the press plate 32) from an operator performing radiographic imaging and ultrasound imaging. The operation panel 44 is, for example, provided on the arm 20 of the medical imaging device 10. The operation panel 44 may be a touch panel.

The I/F 46 performs communication of various information with an external system (such as a radiology information system (RIS)) and/or with a console using wireless communication or wired communication. In the medical imaging device 10 of the present exemplary embodiment, acquired radiographic images and/or ultrasound images are transmitted from the I/F 46 to a console and/or to a reading device (such as a viewer).

Next, explanation follows regarding performing radiographic imaging and ultrasound imaging in the medical imaging device 10 of the present exemplary embodiment.

The medical imaging device 10 of the present exemplary embodiment has an imaging mode to perform consecutive radiographic imaging and ultrasound imaging (referred to below as a "consecutive imaging mode"), and an imaging mode to perform either one from out of radiographic imaging or ultrasound imaging. Explanation follows regarding execution by the medical imaging device 10 of the consecutive imaging mode.

Generally, when performing ultrasound imaging of a breast in a state pressed by the press plate 32, an acoustic matching member is inserted between the press plate 32 and the breast in order to reduce non-uniformity in the impedance to ultrasound waves at the contact plane between the press plate 32 and the breast. In cases in which the consecutive imaging mode is executed in the medical imaging device 10 of the present exemplary embodiment, in order to consecutively perform both radiographic imaging and ultrasound imaging in a state in which the press plate 32 presses the breast all the time until radiographic imaging and ultrasound imaging have been completed, without releasing the pressing of the breast, an acoustic matching member 50 that is not required to perform radiographic imaging is inserted between the press plate 32 and the breast N even during radiographic imaging, as in the example illustrated in FIG. 3.

Figure 4:
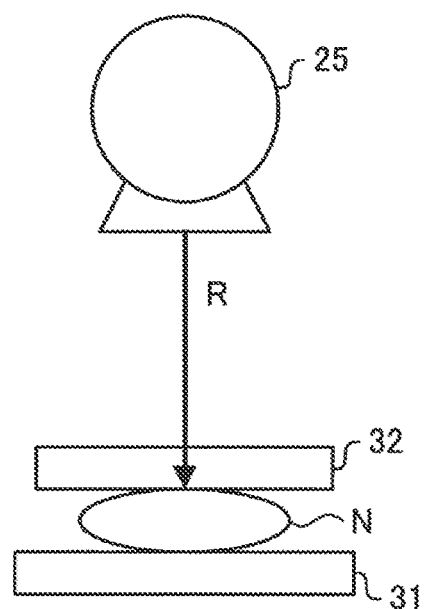
FIG. 4 is a diagram to explain performing radiographic imaging using a medical imaging device of the first exemplary embodiment in a state in which an acoustic matching member has not been provided.

However, as illustrated in the example in FIG. 4, radiographic imaging is performed without providing the acoustic matching member 50 when radiographic imaging (mammography) of a breast is normally performed. In the medical imaging device 10 of the present exemplary embodiment too, the acoustic matching member 50 is not inserted when in an imaging mode that performs radiographic imaging of a breast alone, without performing ultrasound imaging.

The acoustic matching member 50 inserted between the press plate 32 and the breast N in the medical imaging device 10 of the present exemplary embodiment is made of a material that exhibits both good compatibility to a biological object (the breast N in the present exemplary embodiment) and transmissivity to ultrasound waves. The acoustic matching member 50 is preferably formed from a material that is physically strong while being soft, that has good transmissivity to ultrasound waves, and that is also capable of withstanding sterilization treatment. Examples of materials that may be employed as the acoustic matching member 50 include non-water containing gel substances such as urethane rubbers and silicone rubbers, and water containing polymer gels such as polyvinyl alcohols and polyethylene oxides. Note that in order to retain shape, what is referred to as a gel pad, in which the surface of the acoustic matching member 50 is covered by a silicone rubber or the like, is employed as the acoustic matching member 50 in the medical imaging device 10 of the present exemplary embodiment.

The characteristics of the radiation R change due to passing through such the acoustic matching member 50. Thus, the characteristics of the radiation R incident to the breast N is different in cases in which the acoustic matching member 50 has been inserted between the press plate 32 and the breast N to in cases in which the acoustic matching member 50 has not been inserted. For example, in cases in which the radiation R is X-rays, what is referred to as beam hardening occurs in which the energy is shifted to the high energy side by passing through the acoustic matching member 50, and the radiation quality of the radiation R changes. The contrast is decreased of radiographic images imaged when the radiation R has been shifted to the high energy side in this manner. Moreover, for example, dose is reduced of the radiation R incident to the breast N due to the radiation R being absorbed by the acoustic matching member 50.

Note that changes to the radiation quality of the radiation R depend in particular on the thickness of the acoustic matching member 50 at the portion where the radiation R passes through, and there is a greater change in the radiation quality of the radiation R the greater the thickness of the portion of the acoustic matching member 50 passed through. Hence, in the medical imaging device 10 of the present exemplary embodiment, as an example, the type of the acoustic matching member 50 is determined according to the thickness of the portion of the acoustic matching member 50 passed through.

Figure 3:
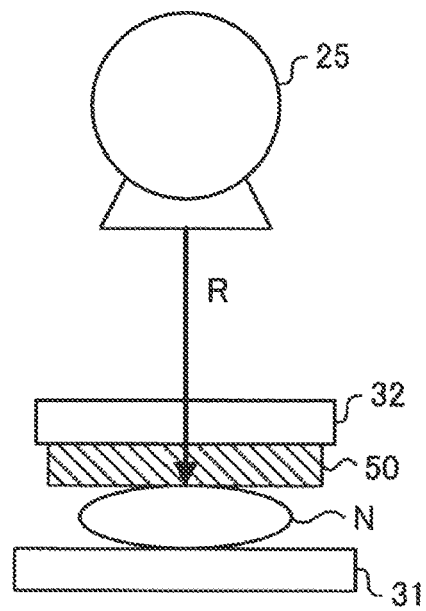
FIG. 3 is a diagram to explain performing radiographic imaging using a medical imaging device of the first exemplary embodiment in a state in which an acoustic matching member has been provided.

The controller 40 of the medical imaging device 10 of the present exemplary embodiment accordingly controls such that the characteristics of the radiation R incident to the breast N (more precisely the radiation quality and the dose) is equivalent, or substantially equivalent, in cases in which radiographic imaging is performed in a state in which the acoustic matching member 50 has been inserted between the press plate 32 and the breast N, as illustrated in the example in FIG. 3, and in cases in which radiographic imaging is performed in a state in which the acoustic matching member 50 has not been inserted between the press plate 32 and the breast N, as illustrated in the example in FIG. 4.

Figure 5:
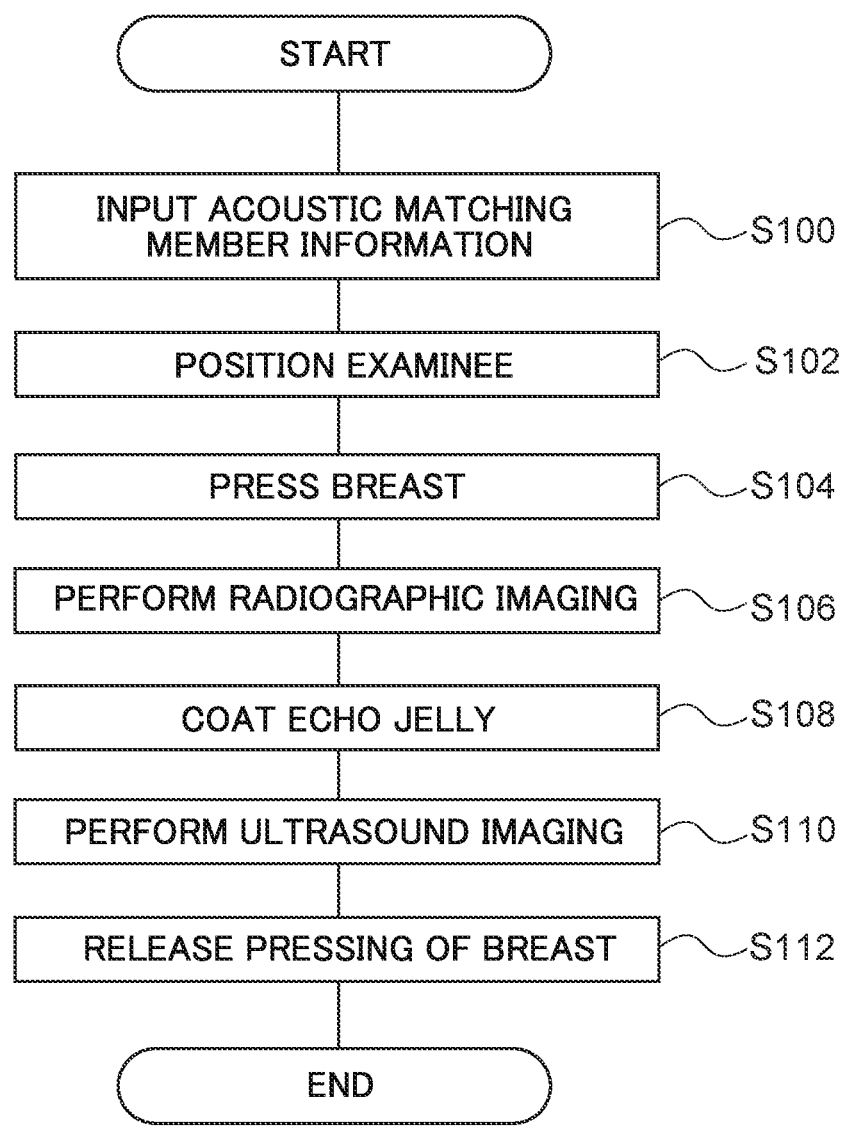
FIG. 5 is a flowchart illustrating an imaging operation in a consecutive imaging mode in which radiographic imaging and ultrasound imaging are performed consecutively by a medical imaging device of the first exemplary embodiment.

FIG. 5 illustrates the overall flow of a chain of an imaging operation in cases in which an operator employs the medical imaging device 10 of the present exemplary embodiment to perform radiographic imaging and ultrasound imaging in the consecutive imaging mode.

First, at step S100, the operator inputs information indicating the type of the acoustic matching member 50 (details are described later) inserted between the breast and the press plate 32 using the operation panel 44 and/or an external device or the like.

At the next step S102, the operator positions the breast N of the examinee on the imaging table 31.

Then, at the next step S104, the medical imaging device 10 presses the breast N of the examinee using the press plate 32 in a state in which the acoustic matching member 50 has been inserted onto the upper surface of the breast N (the surface on the side of the press plate 32). More precisely, at the end of positioning, the operator inputs an instruction through the operation panel 44 to move the press plate 32. The controller 40 presses the breast N in a state sandwiching the acoustic matching member 50 by moving the press plate 32 in the direction to approach the imaging table 31 using the press plate moving mechanism 34 according to the instruction input by the operator.

Note that there are no particular limitations to the method of inserting the acoustic matching member 50 in cases in which the breast N is pressed by the press plate 32. In cases in which it is possible to attach the acoustic matching member 50 to the face of the press plate 32 on the breast side, the breast N may be pressed by the press plate 32 in a state in which the acoustic matching member 50 has been attached to the press plate 32. The breast N may also be pressed by the press plate 32 in a state in which the operator has placed the acoustic matching member 50 on the breast N.

Then, at step S106, the medical imaging device 10 performs radiographic imaging of the breast N by the controller 40 executing radiographic imaging processing (see FIG. 7, details given later). Note that in cases in which radiographic imaging is performed, the controller 40 uses the probe moving mechanism 38 to retract the ultrasound probe 36 to outside of the radiographic image detection region detected by the radiation detector 30.

Figure 6:
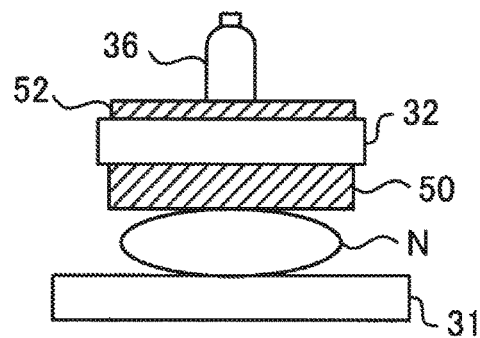
FIG. 6 is a diagram to explain performing ultrasound imaging using a medical imaging device of the first exemplary embodiment.

At the end of radiographic imaging, at the next step S108, the operator coats echo jelly 52 onto the upper face of the press plate 32 (the face on the opposite side to the face where the breast N is disposed), as illustrated in the example in FIG. 6. The echo jelly 52 is also an acoustic matching member. As the echo jelly 52, a low viscosity obstetric gel having, for example, components of distilled water, a moisturizer (at least one of propylene or glycol), a macromolecule polymer, soluble lanolin, a colorant, a perfume, and a preservative (at least one of propylparaben or antiseptic methylparaben), having a neutral pH value in the range of from 6.5 to 7.0, and viscosity from 25000 CPS to 45000 CPS is suitably employed.

Then, at step S110, the medical imaging device 10 performs ultrasound imaging of the breast N. When doing so, as described above, the controller 40 uses the probe moving mechanism 38 to move the ultrasound probe 36 so as to move along the surface of the press plate 32 coated in the echo jelly 52 (the surface facing the radiation tube 26), while detecting the position of the ultrasound probe 36 using the position sensor 37. The controller 40 then performs ultrasound imaging by transmitting ultrasound waves from the ultrasound probe 36 through the breast N, and receiving an ultrasound echo reflected by the interior of the breast N.

At the end of ultrasound imaging, at the next step S112, the medical imaging device 10 releases pressing of the breast N by the press plate 32. More precisely, the operator inputs an instruction through the operation panel 44 to move the press plate 32 (inputs an instruction to release pressing). The controller 40 releases pressing of the breast N by moving the press plate 32 in the direction away from the imaging table 31 using the press plate moving mechanism 34 according to the instruction input by the operator.

When pressing of the breast N has been released in this manner, the imaging operation in the consecutive imaging mode is ended.

Figure 7:
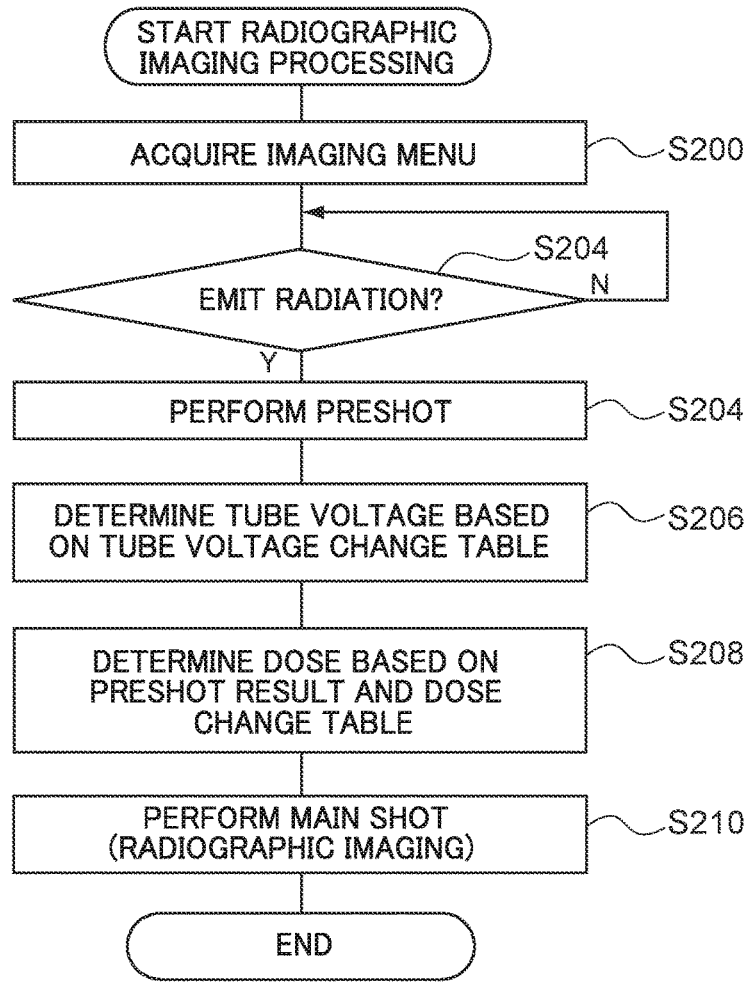
FIG. 7 is a flowchart illustrating a flow of radiographic imaging processing by a medical imaging device of the first exemplary embodiment.

Next, explanation follows regarding radiographic imaging of the present exemplary embodiment executed at the above step S106, with reference to FIG. 7. FIG. 7 is a flowchart of an example of radiographic imaging processing executed by the controller 40 at step S106.

At step S200, the controller 40 acquires an imaging menu. Information, such as information related to the imaging conditions, the examinee, and the breast N, is contained in the imaging menu. For example, the controller 40 may acquire the imaging menu from an external system or the like through the I/F 46, or may acquire the imaging menu input by the operator through the operation panel 44.

At the next step S202, the controller 40 determines whether or not to emit radiation R. In the medical imaging device 10 of the present exemplary embodiment, the operator instructs radiation from a device external to the medical imaging device 10 (for example, from a console, and/or from a device provided with a dedicated switch to instruct radiation of the radiation R) or the like. On receipt of a radiation instruction from such an external device or the like, the controller 40 determines (determines in the affirmative) to emit the radiation R. In cases in which negative determination is made here, a standby state is adopted, and when affirmative determination is made, processing transitions to step S204.

At step S204, the controller 40 performs a preshot by emitting the radiation R from the radiation emitter 25. In order to obtain a radiographic image with an appropriate contrast, in the preshot of the present exemplary embodiment the radiation R is radiated for the purpose of estimating an appropriate integral of tube current over time Q (dose) of the radiation R to be radiated from the radiation emitter 25 onto the breast N during the main shot. Main shot refers to the radiation of the radiation R onto the breast N for the purpose of acquiring radiographic images for use in examination and diagnosis.

At the next step S206, the controller 40 determines the tube voltage for the main shot based on the tube voltage change table 42A. As described above, the radiation quality of the radiation R changes due to passing through the acoustic matching member 50. The radiation quality of the radiation R changes according to the tube voltage. Hence, by adjusting the tube voltage in the medical imaging device 10 of the present exemplary embodiment, the radiation quality in cases in which the radiation R is incident to the breast N after passing through the acoustic matching member 50 is made equivalent to the radiation quality in cases in which the radiation R is incident to the breast N after not passing through the acoustic matching member 50. In the present exemplary embodiment, reference to "equivalent" means within a range that can be taken as being equivalent, including measurement errors and a permissible range.

Namely, by making the tube voltage different in the medical imaging device 10 of the present exemplary embodiment, the radiation quality of the radiation R for imaging the same breast N is made equivalent in cases in which radiographic imaging is performed in the consecutive imaging mode, and the imaging mode that performs radiographic imaging alone. In the present exemplary embodiment, the tube voltage when performing radiographic imaging alone corresponds to a first tube voltage, and the tube voltage when radiographic imaging is performed in the consecutive imaging mode corresponds to a second tube voltage.

More precisely, in the medical imaging device 10 of the present exemplary embodiment, the half value layer of the radiation R is made equivalent by making the tube voltages different. Thus, in the present exemplary embodiment, for example, the tube voltage in cases in which radiographic imaging is performed alone is taken as the tube voltage prior to changing, the tube voltage in cases in which radiographic imaging is performed in the consecutive imaging mode is taken as the tube voltage after changing, and correspondence relationships are obtained in advance between the tube voltage prior to changing, the type of acoustic matching member 50, and the tube voltage after changing giving an equivalent half value layer of the radiation R. FIG. 8 illustrates the tube voltage change table 42A that is an example of correspondence relationships between tube voltage prior to change and tube voltage after changing giving an equivalent half value layer of the radiation R. Although in the present exemplary embodiment the tube voltage change table 42A is stored in the storage unit 42 in advance, as described above, the appropriate tube voltage change table 42A may be acquired from an external device or the like in cases in which the consecutive imaging mode is executed.

As illustrated in FIG. 8, the tube voltage change table 42A indicates correspondence relationships between device specific tube voltages prior to changing, the model number (an example of type) of the acoustic matching member 50, and the tube voltage after changing, that give an equivalent half value layer. Note that although, for ease of explanation, the tube voltage change table 42A illustrated in FIG. 8 lists "device specific half value layers", the "device specific half value layers" do not need to be included in the tube voltage change table 42A. Note that although in the tube voltage change table 42A illustrated in FIG. 8, the tube voltage after changing is associated with the tube voltage prior to changing and the type (model number) of the acoustic matching member 50, rather than the tube voltage after changing itself, a correction value to correct the tube voltage prior to changing may be associated therewith.

More precisely, the controller 40 acquires the type of the acoustic matching member 50 input by the operator at step S100 in the flow of the imaging operation in the consecutive imaging mode described above (see FIG. 5), and acquires the tube voltage (the tube voltage prior to changing) from the imaging menu acquired at step S200. Then, at step S206, the controller 40 determines the tube voltage corresponding to the acquired type of the acoustic matching member 50 and the acquired tube voltage prior to changing, based on the tube voltage change table 42A, and sets the determined tube voltage in the radiation emitter 25.

At the next step S208, the controller 40 determines the dose of the radiation R based on the results of the preshot and the dose change table 42B. As described above, the dose of the radiation R is changed by passing through the acoustic matching member 50. Hence, by adjusting the dose in the medical imaging device 10 of the present exemplary embodiment, the dose (mAs value) of the radiation R in cases in which the radiation R is incident to the breast N after passing through the acoustic matching member 50 is equivalent to the dose of the radiation R in cases in which the radiation R is incident to the breast N after not passing through the acoustic matching member 50. Note that there are no particular limitations to the method by which the dose is adjusted, as long as at least one out of the tube current or the radiation time is adjusted. Note that from the perspective of suppressing the time the breast N of the examinee is pressed, the dose is preferably adjusted by adjusting the tube current.

More precisely, as an example of the present exemplary embodiment, correspondence relationships between the tube voltage after changing, the type of the acoustic matching member 50, and a dose correction value are obtained in advance. FIG. 9 illustrates the dose change table 42B that is an example of correspondence relationships between the tube voltage after changing, the type of the acoustic matching member 50, and a dose correction value. In the present exemplary embodiment, as described above, the dose change table 42B is pre-stored in the storage unit 42; however, the dose change table 42B may be acquired from an external device or the like when the consecutive imaging mode is executed.

As illustrated in FIG. 9, the dose change table 42B indicates correspondence relationships between the tube voltage after changing, the model number (an example of type) of the acoustic matching member 50, and a dose correction coefficient (an example of a dose correction value). Note that the dose correction coefficient in the dose change table 42B of the present exemplary embodiment is a reciprocal of the transmissivity of the radiation R through the acoustic matching member 50. Note that although in the dose change table 42B illustrated in FIG. 9, the dose correction coefficient is associated with tube voltage after changing and the type (model number) of the acoustic matching member 50, rather than the dose correction coefficient, the tube voltage itself after changing may be associated therewith.

More precisely, the controller 40 takes the tube voltage determined at step S206 as the tube voltage after changing and determines the dose correction coefficient corresponding to the tube voltage after changing and the type of the acoustic matching member 50 based on the dose change table 42B. The dose of the main shot is determined by correcting the dose derived from the preshot results with the determined dose correction coefficient, and the determined corrected dose is set in the radiation emitter 25.

At the next step S210, the controller 40 performs the main shot by causing the radiation R to be emitted from the radiation emitter 25. More precisely, the controller 40 performs the main shot by causing radiation to be emitted from the radiation emitter 25 according to the tube voltage determined at step S206 and the dose determined at step S208. Then, after radiographic imaging of the breast N has been performed using the radiation detector 30, the controller 40 ends the present radiographic imaging processing.

Second Exemplary Embodiment

Next, explanation follows regarding a second exemplary embodiment. Parts similar to those of a radiographic imaging system 1 according to the first exemplary embodiment are appended with the same reference numerals, and detailed explanation thereof is omitted.

Configuration of a radiographic imaging system 1 is similar to that of the radiographic imaging system 1 of the first exemplary embodiment (see FIG. 1 and FIG. 2) and so explanation thereof is omitted.

In the present exemplary embodiment, the method of acquiring the type of the acoustic matching member 50 differs to that of the radiographic imaging system 1. In the first exemplary embodiment, the operator inputs the type of the acoustic matching member 50, as illustrated by step S100 in the flow of an imaging operation in the consecutive imaging mode (see FIG. 5), and the controller 40 acquires the input type of the acoustic matching member 50. However, in the medical imaging device 10 of the present exemplary embodiment, the controller 40 acquires the type of the acoustic matching member 50 automatically without operator input.

Figure 10:
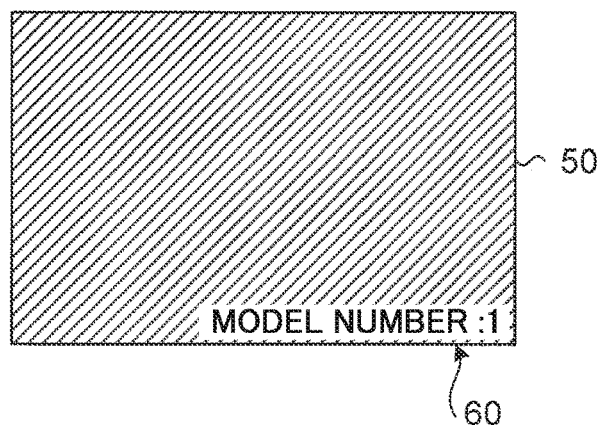
FIG. 10 is diagram to explain an acoustic matching member having a marker.

The acoustic matching member 50 of the present exemplary embodiment includes a marker indicating information to identify the type of the acoustic matching member 50. In the example illustrated in FIG. 10, the acoustic matching member 50 includes a marker 60 indicating the type (model number) of the acoustic matching member 50 at one location from out of the corners (corner portions) of the acoustic matching member 50. There are no particular limitations to the substance and so on of the marker 60, and it is sufficient that the substance of the marker 60 is a substance recognizably imaged in radiographic imaging, and is a substance having a different transmissivity to the acoustic matching member 50 and the radiation R. The position where the marker 60 is disposed at one location from the four corners of the acoustic matching member 50 is not limited to that of the example illustrated in FIG. 10, and is not particularly limited; however, it is preferably a position not overlapping with the image of the breast N.

The controller 40 of the medical imaging device 10 in the present exemplary embodiment acquires the type of the acoustic matching member 50 based on the distinguishing results from distinguishing the image of the marker 60 in the radiographic image obtained by the preshot.

Figure 11:
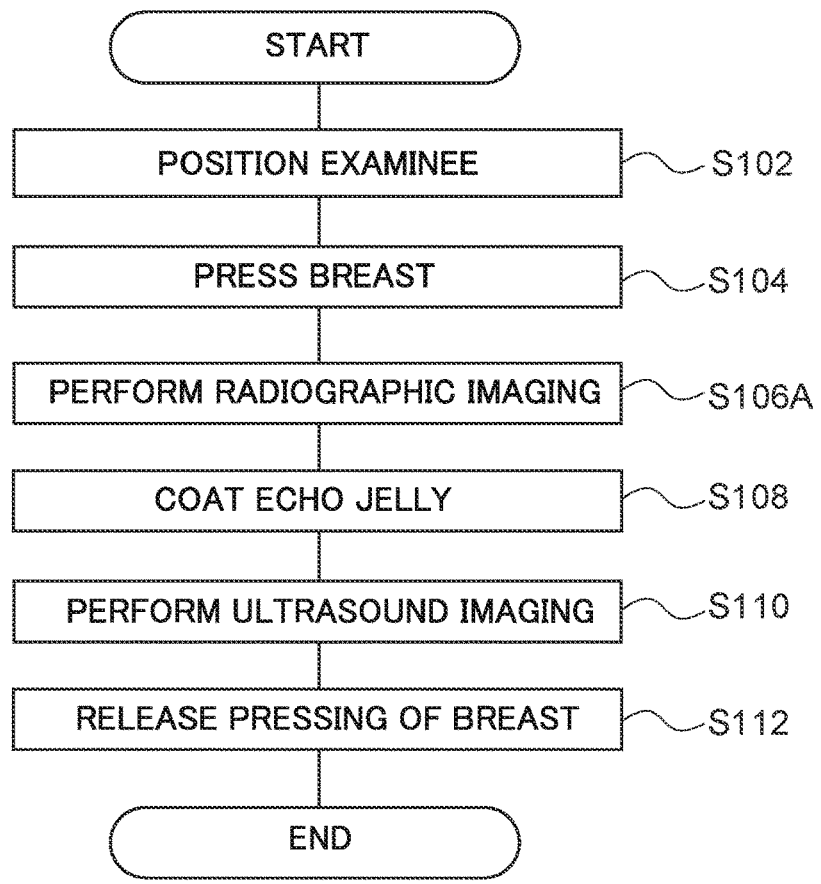
FIG. 11 is a flowchart illustrating an imaging operation in a consecutive imaging mode in which radiographic imaging and ultrasound imaging are performed consecutively by a medical imaging device of a second exemplary embodiment.

Hence, as illustrated in FIG. 11, the imaging operation in the consecutive imaging mode in the medical imaging device 10 of the present exemplary embodiment is different to the imaging operation of the consecutive imaging mode in the medical imaging device 10 of the first exemplary embodiment (see FIG. 5), in the point that step S100 is not executed.

Moreover, as illustrated in FIG. 11, in the imaging operation in the consecutive imaging mode of the medical imaging device 10 of the present exemplary embodiment, step S106A is executed in place of step S106 of the imaging operation of the consecutive imaging mode of the first exemplary embodiment (see FIG. 5).

Figure 12:
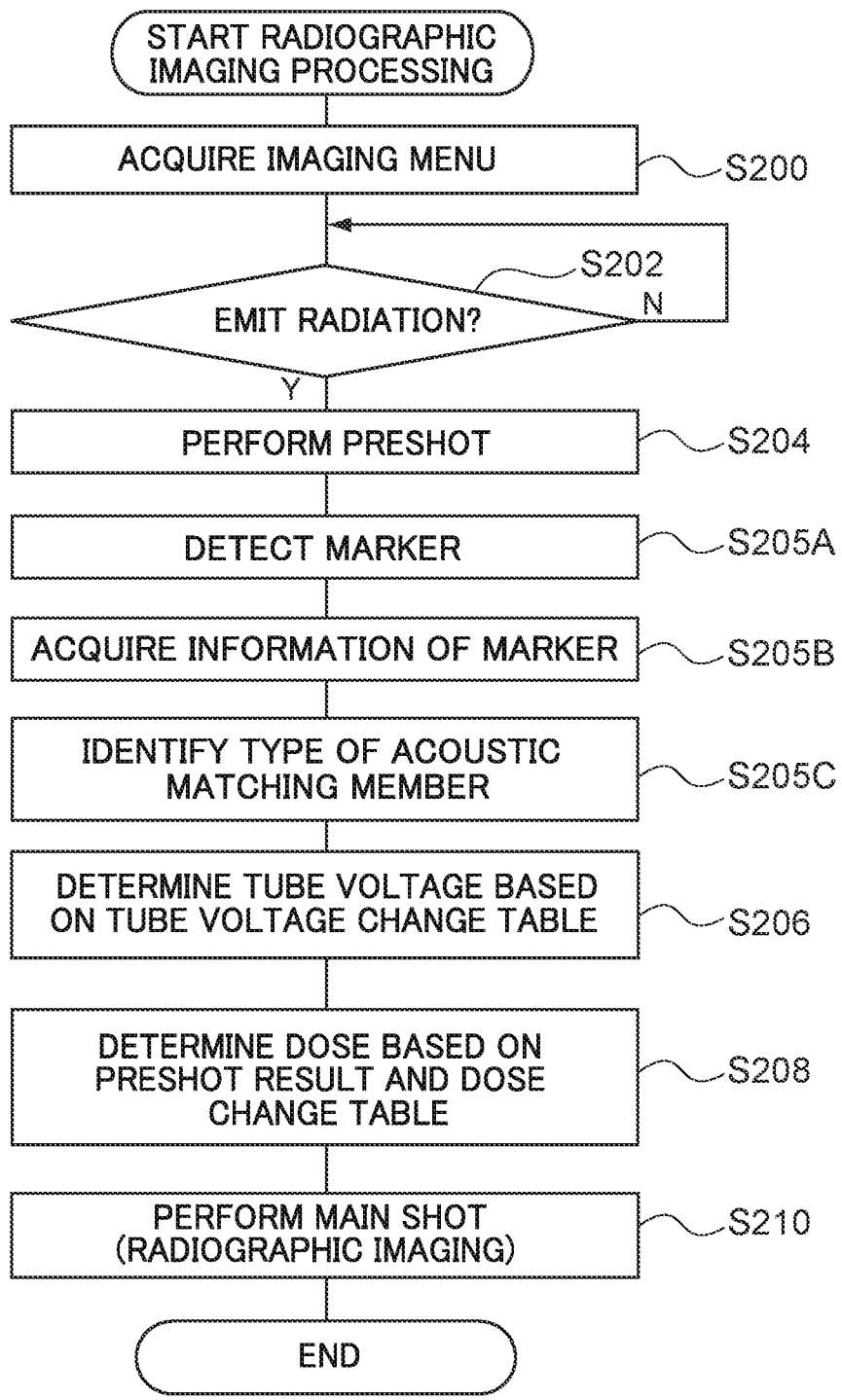
FIG. 12 is a flowchart illustrating a flow of radiographic imaging processing by a medical imaging device of the second exemplary embodiment.

Explanation follows regarding performing radiographic imaging in the present exemplary embodiment by executing step S106A of the consecutive imaging mode using the medical imaging device 10 of the present exemplary embodiment, with reference to FIG. 12. FIG. 12 is a flowchart of an example of radiographic imaging processing executed by the controller 40 at step S106A.

The radiographic imaging processing of the present exemplary embodiment differs from that of the first exemplary embodiment in the point that the processing of steps S205A to 5205C is executed between steps S204 and step S206 in the radiographic imaging processing of the first exemplary embodiment (see FIG. 7).

Figure 13:
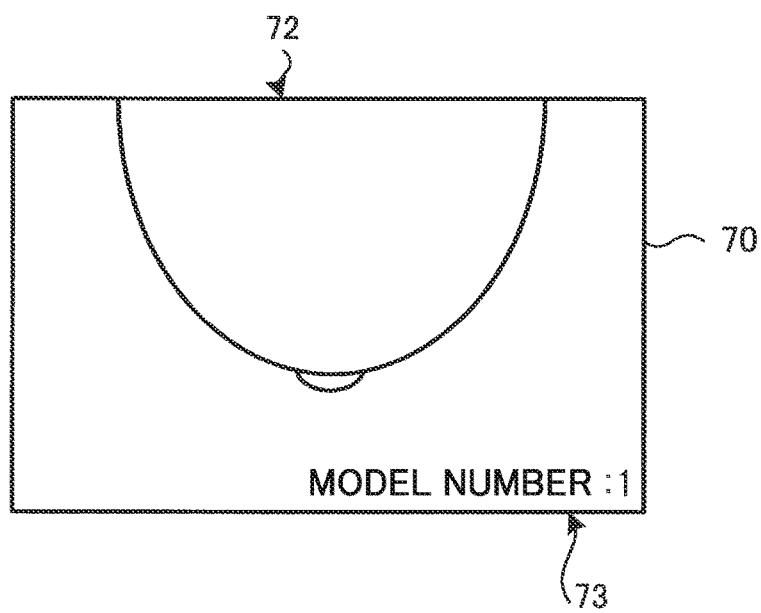
FIG. 13 is diagram to explain a radiographic image obtained by a preshot including an image of a marker.

As illustrated in the example in FIG. 13, a radiographic image 70 obtained by the preshot executed at step S204 contains a breast N image 72, and a marker image 73.

Thus at step S205A, the controller 40 detects the marker image 73 in the radiographic image 70 obtained by the preshot. Note that the method of detecting the marker image 73 is not particularly limited, and the marker may be detected by performing image analysis or the like.

At the next step S205B, the controller 40 obtains information of the marker 60 based on the detected marker image 73. Then at the next step S205C, the controller 40 acquires the type of the acoustic matching member 50 by identifying the type of the acoustic matching member 50 based on the acquired information of the marker 60. The method of acquiring the information of the marker 60 from the marker image 73, and the method of identifying the type of the acoustic matching member 50 based on the information of the marker 60, are not particularly limited. For example, the type of the acoustic matching member 50 may be identified based on information stored in the storage unit 42 indicating correspondence relationships between the information of the marker 60 and the type of each acoustic matching member 50.

Thus, in the medical imaging device 10 of the present exemplary embodiment, imaging is performed in the consecutive imaging mode using the acoustic matching member 50 having the marker 60 indicating information to identify the type of the acoustic matching member 50. The controller 40 then detects the marker image 73 in the radiographic image 70 obtained by the preshot, acquires the information of the marker 60, and acquires the type of the acoustic matching member 50 based on the information of the marker 60.

Thereby, according to the medical imaging device 10 of the present exemplary embodiment, due to being able to automatically acquire the appropriate type of the acoustic matching member 50, the operator does not need to input the type of the acoustic matching member 50.

Thereby, according to the medical imaging device 10 of the present exemplary embodiment, due to being able to automatically acquire the appropriate type of the acoustic matching member 50, there is no need for the operator to input the type of the acoustic matching member 50.

Note that preferably the controller 40 gives a warning to the operator in the following cases. Namely, in cases in which it has not been possible for the controller 40 to detect the marker image 73 from the radiographic image 70 obtained by the preshot, in cases in which it has not been possible to acquire the information of the marker 60 even though the marker image 73 has been detected, and in cases in which there was no type of acoustic matching member 50 associated with the acquired marker 60 information, for example, such as by displaying the situation on the operation panel 44.

Note that although in the medical imaging device 10 of the present exemplary embodiment, the radiographic image 70 from imaging the marker 60 on the acoustic matching member 50 in the preshot is employed in order for the controller 40 to automatically acquire the type of the acoustic matching member 50, there is no limitation thereto, and an image obtained by another method may be employed therefor.

Figure 14:
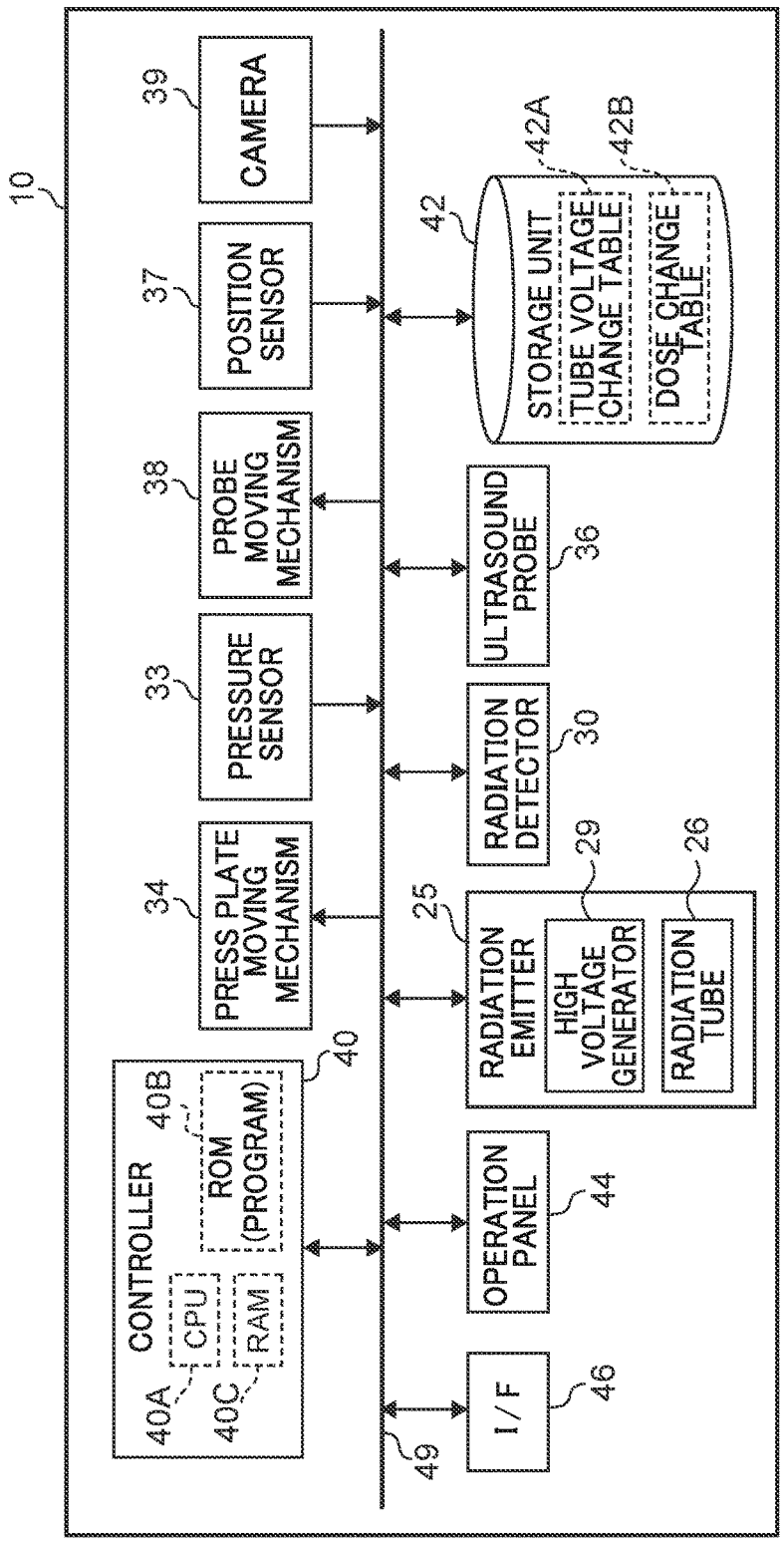
FIG. 14 is a block diagram illustrating a configuration of a medical imaging device equipped with a camera for imaging a marker.
Figure 15:
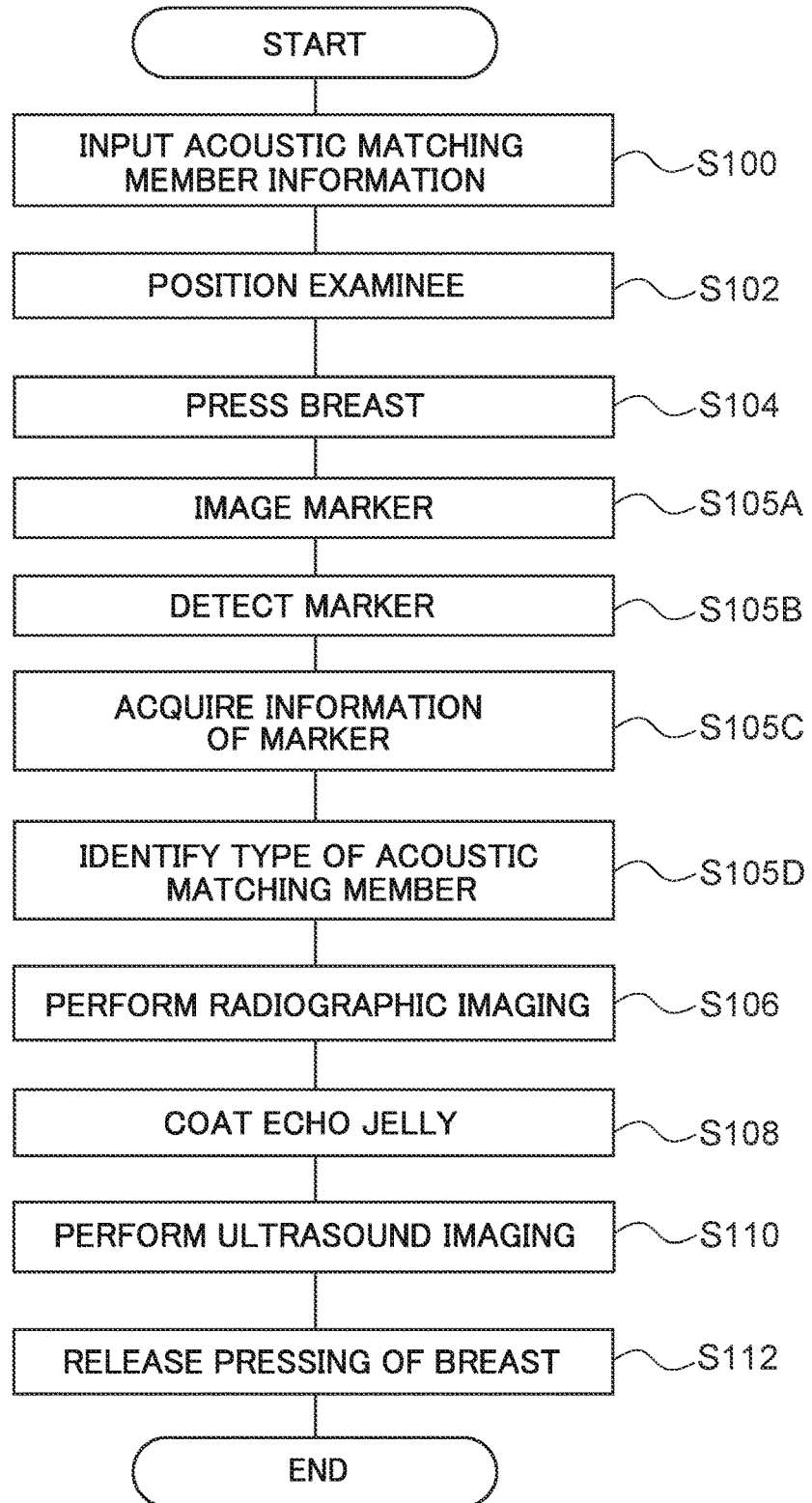
FIG. 15 is a flowchart illustrating an imaging operation in a consecutive imaging mode in which radiographic imaging and ultrasound imaging are performed consecutively by the medical imaging device illustrated in FIG. 4.

For example, an image of the breast N may be imaged without emitting radiation R from the radiation emitter 25, and images imaged by a normal camera (an ordinary digital camera) may be employed. In such cases, the medical imaging device 10 further includes a camera 39 as an imaging section for imaging the marker 60 on the acoustic matching member 50, as illustrated in FIG. 14. Moreover, as an example, operation of the consecutive imaging mode is executed in the medical imaging device 10 as illustrated in FIG. 15. The imaging operation of the consecutive imaging mode illustrated in FIG. 15 differs from the imaging operation of the consecutive imaging mode in the medical imaging device 10 of the present exemplary embodiment (see FIG. 5) in the point that performing of steps S105A to S105D is executed between step S104 and step S106.

At step S105A as illustrated in FIG. 15, the controller 40 images the marker 60 on the acoustic matching member 50 using the camera 39. The imaging performed here does not need to image the breast N, as long as the marker 60 is imaged. At the next step S105B, the controller 40 detects the image of the marker in the image obtained using the camera 39. Note that there is no particular limitation to the method of detecting the image of the marker, and detection may be performed by image analysis or the like. At the next step S105C, the controller 40 acquires information of the marker 60 based on the detected marker image. Then at the next step S105D, the controller 40 acquires the type of the acoustic matching member 50 by identifying the type of the acoustic matching member 50 based on the acquired information of the marker 60. There are no particular limitations to the method of acquiring the information of the marker 60 from the marker image, or to the method of identifying the type of the acoustic matching member 50 based on the information of the marker 60, and they may be similar to cases in which the radiographic image 70 obtained by the preshot is employed.

Thus, according to the imaging operation of the consecutive imaging mode illustrated in FIG. 15, the controller 40 is able to automatically acquire the type of the acoustic matching member 50 by employing an image imaged by the camera 39. In such cases, the medical imaging device 10 needs to be equipped with the camera 39, and there is a concern that the camera 39 might break due to emission of the radiation R by the radiation emitter 25. Moreover, a process to image the marker 60 using the camera 39 is added in addition to imaging the radiographic image of the breast N using the radiation detector 30. Hence, as described above, the medical imaging device 10 preferably employs a radiographic image imaged by the preshot for the controller 40 to automatically acquire the type of the acoustic matching member 50.

The medical imaging devices 10 of the exemplary embodiments explained above include the press plate 32 for pressing the breast N and the radiation emitter 25 for radiating the radiation R onto the breast N, and are medical imaging devices capable of performing radiographic imaging and ultrasound imaging of the breast N. The controller 40 of the medical imaging device 10 acquires various information indicating the type of the acoustic matching member 50 inserted between the press plate 32 and the breast N in cases in which ultrasound imaging of the breast N is being performed. Moreover, the controller 40 sets the tube voltage of the radiation emitter 25 to the first tube voltage in cases in which radiographic imaging alone is being performed on the breast N, and sets the tube voltage of the radiation emitter 25 to the second tube voltage that is different from the first tube voltage by using the various information acquired in cases in which radiographic imaging and ultrasound imaging is performed on the breast N consecutively with the acoustic matching member 50 still inserted.

Thus, according to the medical imaging devices 10 of the above exemplary embodiments, suitable radiographic imaging can be performed that takes into consideration the type of the acoustic matching member 50 being employed.

Note that although in the above exemplary embodiments, the type of the acoustic matching member 50 is determined according to the thickness of the acoustic matching member 50 at a part through which the radiation R passes, the determination of the type of the acoustic matching member 50 is not limited thereto. The type of the acoustic matching member 50 may be determined according to the shape and material, etc. of the acoustic matching member 50, or may be determined according to factors that influence the characteristics of radiation R passing through the acoustic matching member 50. The type of the acoustic matching member 50 may also be categorized and set according to these factors. Note that changes to the characteristics of the radiation R depend particularly on the thickness of the acoustic matching member 50, and so in cases in which the type of the acoustic matching member 50 is not determined according to the thickness thereof, the controller 40 preferably acquires the type and thickness of the acoustic matching member 50, and adjusts the tube voltage according to the type and thickness of the acoustic matching member 50.

Moreover, although in the above exemplary embodiments, the acoustic matching member 50 is only provided between the breast N and the press plate 32 when performing radiographic imaging in the consecutive imaging mode, an acoustic matching member such as the echo jelly 52 may also be provided on the upper face of the press plate 32 (the face on the opposite side to the face where the acoustic matching member 50 is provided), or an acoustic matching member such as the echo jelly 52 may only be provided on the upper face of the press plate 32. In such cases, the tube voltage of the radiation tube 26 may be set according to the type of all of the acoustic matching members provided.

Figure 16:
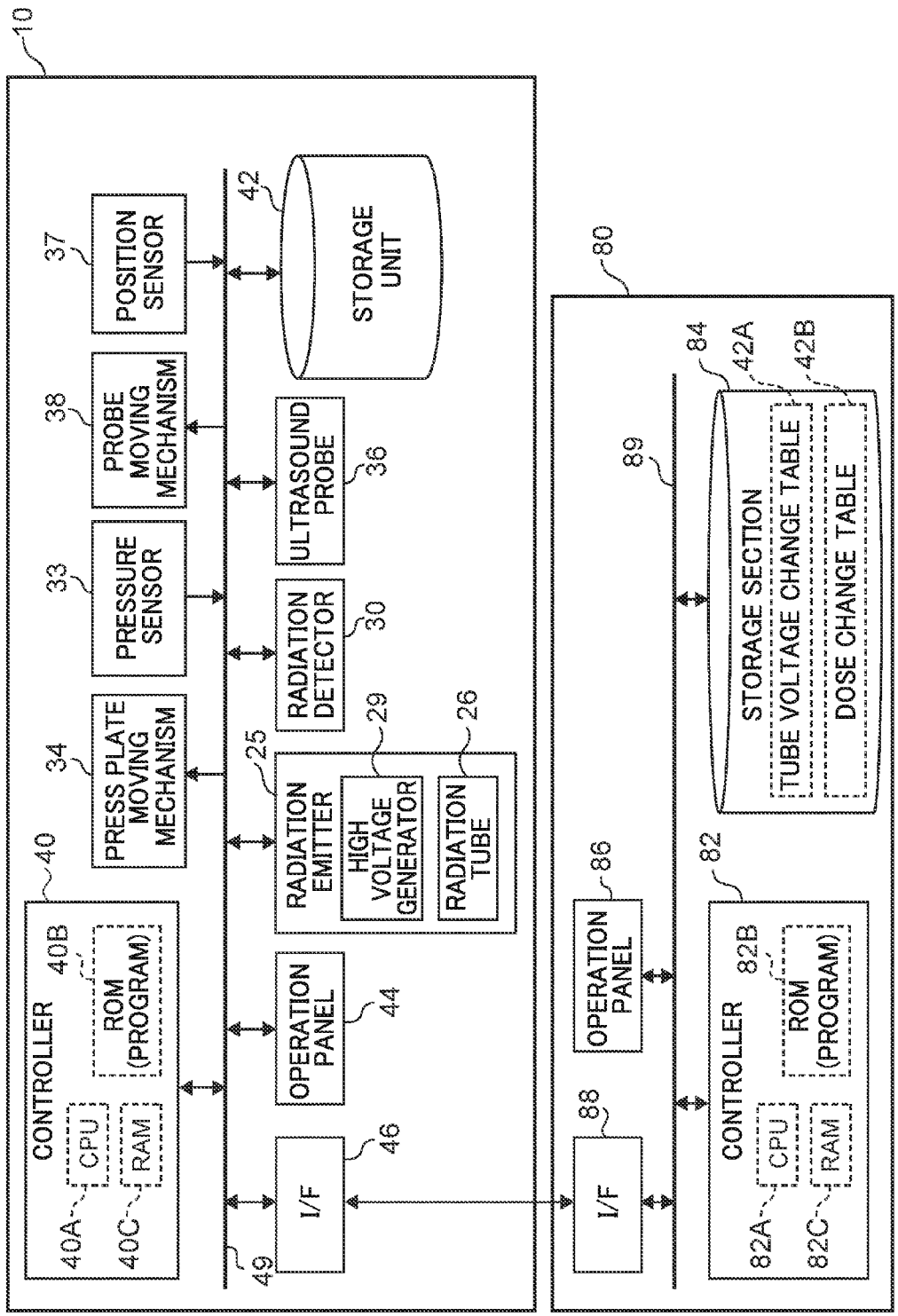
FIG. 16 is a block diagram illustrating a configuration of a tube voltage setting device and a medical imaging device.

Moreover, although in the above exemplary embodiments it is the controller 40 of the medical imaging device 10 that sets the tube voltage and dose in cases in which radiographic imaging is performed in the consecutive imaging mode, the setting may be performed by something other than the controller 40. For example, a tube voltage setting device provided separately to the medical imaging device 10 may perform the setting. FIG. 16 illustrates a block diagram of an example of a configuration of a medical imaging device 10 and a tube voltage setting device 80 in such a case. As illustrated in FIG. 16, the tube voltage setting device 80 includes a controller 82, a storage unit 84, an operation panel 86, and an I/F 88. The controller 82, the storage unit 84, the operation panel 86, and the I/F 88 are connected together by a bus 89, such as a system bus or a control bus, so as to be capable of exchanging various signals with each other.

The controller 82 controls the overall operation of the tube voltage setting device 80, and sets imaging conditions, such as the tube voltage and tube current, etc. in the radiation emitter 25 of the medical imaging device 10. The controller 82 includes a CPU 82A, ROM 82B, and RAM 82C. Various programs, etc. to be executed by the CPU 82A are pre-stored in the ROM 82B. The RAM 82C temporarily stores various data.

The above-described tube voltage change table 42A and dose change table 42B are stored in the storage unit 84. Hence, as illustrated in FIG. 16, the tube voltage change table 42A and the dose change table 42B are not stored in the storage unit 42 of the medical imaging device 10. The operation panel 86 is a touch panel or the like, and is employed when an operator inputs information indicating the type of the acoustic matching member 50. The I/F 88 performs communication of various information with an external system (such as an RIS) or the like, and with the medical imaging device 10 using wireless communication or wired communication.

The controller 82 of the tube voltage setting device 80 acquires various information indicating the type of the acoustic matching member 50 that is disposed between the ultrasound probe and the breast N during ultrasound imaging of the breast N, and that is present between the radiation emitter 25 and the breast N during radiographic imaging of the breast N. Moreover, the controller 82 sets the tube voltage of the radiation tube 26 of the radiation emitter 25 according to the type indicated by the acquired various information when performing radiographic imaging of the breast N. The controller 82 also sets the dose of the radiation R emitted from the radiation tube 26 of the radiation emitter 25 according to the type indicated by the acquired various information.

The method employed by the controller 82 to set the tube voltage and dose may, for example, be similar to the method employed by the controller 40 of the medical imaging device 10 in the above exemplary embodiments. For example, similarly to in the first exemplary embodiment as described above, information may be acquired indicating the type of the acoustic matching member 50 that has been input by an operator, and the tube voltage and dose, which have been determined according to the type of acoustic matching member 50 by employing the tube voltage change table 42A and the dose change table 42B stored in the storage unit 84, may be set in the radiation emitter 25 through the I/F 88 and the I/F 46. Moreover, similarly to in the second exemplary embodiment, the radiographic image 70 obtained by the preshot may be acquired from the medical imaging device 10, and the marker image 73 detected in the radiographic image 70, the information of the marker 60 acquired, and the type of the acoustic matching member 50 acquired based on the information of the marker 60. Moreover, an image obtained by imaging the marker 60 using the camera 39 may be acquired from the medical imaging device 10, a marker image detected in the image, the information of the marker 60 acquired, and the type of the acoustic matching member 50 acquired based on the information of the marker 60.

Note what is referred to as a console may be employed, or a dedicated controller device for the radiation emitter 25, may be employed as such a tube voltage setting device 80. Moreover, the tube voltage setting device 80 may be provided on the arm 20 of the medical imaging device 10.

There are no particular limitations to the radiation R in the above exemplary embodiments, and X-rays, gamma rays, etc. may be employed therefor.

The configuration, operation, and the like of the medical imaging device 10, etc. explained in the above exemplary embodiments are merely examples thereof, and various modifications are possible according to the circumstances within a range not departing from the spirit of the invention.

An object of the present disclosure is to provide a medical imaging device, a tube voltage setting device, an imaging control method, and a recording medium storing an imaging control program capable of performing suitable radiographic imaging that takes into consideration the type of acoustic matching member employed.

In order to achieve the above object, a medical imaging device of the present disclosure includes a press plate that presses a breast, an emitter that radiates radiation onto the breast, an acquisition section that acquires various information indicating a type of an acoustic matching member inserted between the press plate and the breast in cases in which ultrasound imaging of the breast is performed, and a setting section. The setting section sets a tube voltage of the emitter to a first tube voltage in cases in which radiographic imaging of the breast is performed alone, and that sets the tube voltage of the emitter to a second tube voltage different from the first tube voltage by employing the various information acquired by the acquisition section in cases in which radiographic imaging and ultrasound imaging of the breast are performed consecutively with the acoustic matching member still inserted.

The setting section of the medical imaging device of the present disclosure may be configured to further set a dose of radiation emitted from a radiation tube of the emitter according to the type indicted by the various information.

The setting section of the medical imaging device of the present disclosure may be configured to determine the dose to set based on information indicating a correspondence relationship between type of the acoustic matching member and dose of the radiation or correction values of the dose.

The medical imaging device of the present disclosure may be configured such that the acoustic matching member is applied with a marker corresponding to the various information, the medical imaging device further includes an imaging section that images the marker, and the acquisition section acquires the various information based on an image of the marker imaged by the imaging section.

The medical imaging device of the present disclosure may be configured such that the acoustic matching member is applied with a marker that has a different transmissivity to radiation to that of the acoustic matching member and that corresponds to the various information, and the acquisition section radiates radiation from the emitter onto the marker and acquires the various information based on a radiographic image of the marker that has been imaged.

The medical imaging device of the present disclosure may be configured such that the type of the acoustic matching member is determined according to a thickness of a part of the acoustic matching member through which radiation emitted from the emitter passes.

The setting section of the medical imaging device of the present disclosure may be configured to determine the tube voltage to set based on information indicating a correspondence relationship between type of the acoustic matching member and a tube voltage of the radiation tube or a correction value of the tube voltage.

The medical imaging device of the present disclosure may be configured such that the tube voltage or the correction value of the tube voltage makes a half value layer of radiation passing through the acoustic matching member and incident to the breast the same as a half value layer of radiation not passing through the acoustic matching member and incident to the breast.

The medical imaging device of the present disclosure may be configured such that, for cases in which radiographic imaging and ultrasound imaging of the breast are performed consecutively with the acoustic matching member still inserted, in cases in which a different acoustic matching member to the acoustic matching member is further provided between the press plate and the emitter, the acquisition section further acquires various information indicating a type of the different acoustic matching member, and the setting section sets the tube voltage of the emitter using the various information of the acoustic matching member and various information of the different acoustic matching member acquired by the acquisition section.

The press plate of the medical imaging device of the present disclosure may be configured to keep the breast in a pressed state until the radiographic imaging and ultrasound imaging have ended in cases in which radiographic imaging and ultrasound imaging of the breast are performed consecutively with the acoustic matching member still inserted.

In order to achieve the above object, a tube voltage setting device of the present disclosure includes: an acquisition section that acquires various information indicating a type of an acoustic matching member disposed between an ultrasound probe and a breast in cases in which ultrasound imaging of the breast is performed, and present between a radiation emitter and the breast in cases in which radiographic imaging of the breast is performed; and a setting section that sets a tube voltage of a radiation tube of the radiation emitter according to the type indicated by the various information acquired by the acquisition section in cases in which radiographic imaging of the breast is performed.

In order to achieve the above object, an imaging control method of the present disclosure is an imaging control method for a medical imaging device equipped with a press plate to press a breast and an emitter to radiate radiation onto the breast, and capable of performing radiographic imaging and ultrasound imaging of the breast. The imaging control method includes: acquiring various information indicating a type of an acoustic matching member inserted between the press plate and the breast in cases in which ultrasound imaging of the breast is performed; setting a tube voltage of the emitter to a first tube voltage in cases in which radiographic imaging of the breast is performed alone; and setting the tube voltage of the emitter to a second tube voltage different from the first tube voltage by employing the acquired various information in cases in which radiographic imaging and ultrasound imaging of the breast are performed consecutively with the acoustic matching member still inserted.

In order to achieve the above object, a non-transitory recording medium of the present disclosure stores a program that causes a computer to execute an imaging control process for a medical imaging device equipped with a press plate to press a breast and an emitter to radiate radiation onto the breast, and capable of performing radiographic imaging and ultrasound imaging of the breast. The process includes: acquiring various information indicating a type of an acoustic matching member inserted between the press plate and the breast in cases in which ultrasound imaging of the breast is performed; setting a tube voltage of the emitter to a first tube voltage in cases in which radiographic imaging of the breast is performed alone; and setting the tube voltage of the emitter to a second tube voltage different from the first tube voltage by employing the acquired various information in cases in which radiographic imaging and ultrasound imaging of the breast are performed consecutively with the acoustic matching member still inserted.

The present disclosure can provide a medical imaging device, a tube voltage setting device, an imaging control method, and a recording medium storing an imaging control program capable of performing suitable radiographic imaging that takes into consideration the type of acoustic matching member employed.

What is claimed is:

1. A medical imaging device comprising:
   a press plate that presses a breast;
   an emitter that radiates radiation onto the breast;
   an acquisition section that acquires various information indicating a type of an acoustic matching member inserted between the press plate and the breast in cases in which ultrasound imaging of the breast is performed; and
   a setting section that sets a tube voltage of the emitter to a first tube voltage, in cases in which radiographic imaging of the breast is performed alone, and that sets the tube voltage of the emitter to a second tube voltage that is different from the first tube voltage, by employing the various information acquired by the acquisition section, in cases in which radiographic imaging and ultrasound imaging of the breast are performed consecutively with the acoustic matching member still inserted.

2. The medical imaging device of claim 1, wherein the setting section further sets a dose of radiation emitted from a radiation tube of the emitter according to the type indicated by the various information.

3. The medical imaging device of claim 2, wherein the setting section determines the dose of radiation based on information indicating a correspondence relationship between the type of the acoustic matching member and the dose of radiation or correction values of the dose.

4. The medical imaging device of claim 1, wherein:
   the acoustic matching member is applied with a marker corresponding to the various information;
   the medical imaging device further includes an imaging section that images the marker; and
   the acquisition section acquires the various information based on an image of the marker imaged by the imaging section.

5. The medical imaging device of claim 1, wherein:
   the acoustic matching member is applied with a marker that has a differenttransmissivity to radiation from that of the acoustic matching member and that corresponds to the various information; and
   the acquisition section radiates radiation from the emitter onto the marker and acquires the various information based on a radiographic image of the marker that has been imaged.

6. The medical imaging device of claim 1, wherein:
   the type of the acoustic matching member is determined according to a thickness of a part of the acoustic matching member through which radiation emitted from the emitter passes.

7. The medical imaging device of claim 1, wherein:
   the setting section determines the tube voltage to set based on information indicating a correspondence relationship between the type of the acoustic matching member and a tube voltage of the radiation tube or a correction value of the tube voltage of the radiation tube.

8. The medical imaging device of claim 7, wherein:
the tube voltage or the correction value of the tube voltage makes a half value layer of radiation passing through the acoustic matching member and incident to the breast the same as a half value layer of radiation not passing through the acoustic matching member and incident to the breast.

9. The medical imaging device of claim 1, wherein:
for cases in which radiographic imaging and ultrasound imaging of the breast are performed consecutively with the acoustic matching member still inserted, and a different acoustic matching member from the acoustic matching member is further provided between the press plate and the emitter:
the acquisition section further acquires various information indicating a type of the different acoustic matching member; and
the setting section sets the tube voltage of the emitter using the various information of the acoustic matching member and the various information of the different acoustic matching member acquired by the acquisition section.

10. The medical imaging device of claim 1, wherein:
the press plate keeps the breast in a pressed state until the radiographic imaging and theultrasound imaging have ended, in cases in which radiographic imaging and ultrasound imaging of the breast are performed consecutively with the acoustic matching member still inserted.

11. A tube voltage setting device comprising:
an acquisition section that acquires various information indicating a type of an acoustic matching member disposed between an ultrasound probe and a breast in cases in which ultrasound imaging of the breast is performed, and present between a radiation emitter and the breast in cases in which radiographic imaging of the breast is performed; and
a setting section that sets a tube voltage of a radiation tube of the radiation emitter according to the type indicated by the various information acquired by the acquisition section in cases in which radiographic imaging of the breast is performed.

12. An imaging control method for a medical imaging device equipped with a press plate to press a breast and an emitter to radiate radiation onto the breast, and capable of performing radiographic imaging and ultrasound imaging of the breast, the imaging control method comprising:
acquiring various information indicating a type of an acoustic matching member inserted between the press plate and the breast in cases in which ultrasound imaging of the breast is performed;
setting a tube voltage of the emitter to a first tube voltage in cases in which radiographic imaging of the breast is performed alone; and
setting the tube voltage of the emitter to a second tube voltage that is different from the first tube voltage, by employing the acquired various information, in cases in which radiographic imaging and ultrasound imaging of the breast are performed consecutively with the acoustic matching member still inserted.

13. A non-transitory recording medium storing a program that causes a computer to execute an imaging control process for a medical imaging device equipped with a press plate to press a breast and an emitter to radiate radiation onto the breast, and capable of performing radiographic imaging and ultrasound imaging of the breast, the process comprising:
acquiring various information indicating a type of an acoustic matching member inserted between the press plate and the breast in cases in which ultrasound imaging of the breast is performed;
setting a tube voltage of the emitter to a first tube voltage in cases in which radiographic imaging of the breast is performed alone; and
setting the tube voltage of the emitter to a second tube voltage that is different from the first tube voltage, by employing the acquired various information, in cases in which radiographic imaging and ultrasound imaging of the breast are performed consecutively with the acoustic matching member still inserted.

* * * * *